(12) United States Patent
Kamada

(10) Patent No.: US 9,271,650 B2
(45) Date of Patent: Mar. 1, 2016

(54) OPHTHALMOLOGIC APPARATUS AND CONTROL METHOD FOR OPHTHALMOLOGIC APPARATUS

(71) Applicant: CANON KABUSHIKI KAISHA, Tokyo (JP)

(72) Inventor: Shohhei Kamada, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 79 days.

(21) Appl. No.: 14/299,291

(22) Filed: Jun. 9, 2014

(65) Prior Publication Data
US 2014/0368791 A1  Dec. 18, 2014

(30) Foreign Application Priority Data
Jun. 17, 2013  (JP) .................................. 2013-126729

(51) Int. Cl.
*A61B 3/14* (2006.01)
*A61B 3/00* (2006.01)
*A61B 3/12* (2006.01)

(52) U.S. Cl.
CPC ................. *A61B 3/12* (2013.01); *A61B 3/0075* (2013.01)

(58) Field of Classification Search
USPC .......................................... 351/206, 208, 246
See application file for complete search history.

(56) References Cited

U.S. PATENT DOCUMENTS

| 2009/0079939 A1 | 3/2009 | Mimura |
| 2009/0195750 A1 | 8/2009 | Isogai et al. |
| 2012/0218519 A1 | 8/2012 | Akiba |
| 2012/0218520 A1 | 8/2012 | Inoue |
| 2012/0218521 A1 | 8/2012 | Dobashi |

FOREIGN PATENT DOCUMENTS

| CN | 101507601 A | 8/2009 |
| CN | 102648842 A | 8/2012 |
| JP | 2001-037722 A | 2/2001 |
| WO | 2013/002332 A1 | 1/2013 |

OTHER PUBLICATIONS

Chinese office action issued in corresponding application No. 201410270593.3 on Sep. 15, 2015.

*Primary Examiner* — Jack Dinh
(74) *Attorney, Agent, or Firm* — Carter, DeLuca, Farrell & Schmidt, LLP

(57) ABSTRACT

Provided is an ophthalmologic apparatus capable of performing an alignment operation between an eye to be inspected and an inspection unit, the ophthalmologic apparatus including: an inspection unit configured to obtain inspection information of an eye to be inspected; a base unit including a support member configured to determine a holding position of the eye to be inspected; an operation unit configured to operate movement of the inspection unit with respect to the base unit in accordance with an operation amount; a moving unit configured to move the inspection unit in accordance with the operation amount input from the operation unit; a detection unit configured to detect a position of the inspection unit with respect to the base unit; and a control unit configured to control an amount related to movement of the inspection unit corresponding to the operation amount based on a detection result of the detection unit.

17 Claims, 7 Drawing Sheets

OPHTHALMOLOGIC APPARATUS AND CONTROL METHOD FOR OPHTHALMOLOGIC APPARATUS

BACKGROUND OF THE INVENTION

1. Field of the Invention

The present invention relates to an ophthalmologic apparatus used in an eye clinic or the like and a control method for the ophthalmologic apparatus.

2. Description of the Related Art

As an ophthalmologic instrument, there is known a fundus camera for performing fundus imaging of an eye to be inspected.

When taking an image of a fundus by the fundus camera, it is necessary to align an imaging portion with a predetermined position with respect to the eye to be inspected. In order to perform this alignment, the following fundus camera is widely known. The fundus camera includes an alignment operation member such as a joystick, and the alignment operation member is operated (tilted, rotated, and the like) so that the imaging portion is moved up and down, front and back, and left and right.

In general, the alignment operation member for the fundus camera performs a rough operation in which the imaging portion is roughly moved in a case where rough alignment is sufficient such as the case of switching the imaging portion between left and right eyes. In addition, the alignment operation member has a mechanism capable of performing fine movement in which the imaging portion is precisely moved when fine alignment with the eye to be inspected is necessary.

In Japanese Patent Application Laid-Open No. 2001-037722, there is disclosed a structure in which a moving amount of the imaging portion per unit operation amount of the alignment operation member is changed in accordance with an alignment deviation amount between the eye to be inspected and the imaging portion. The alignment deviation amount is determined from a deviation between the center of a sighting scale S set in an anterior ocular segment image of the eye to be inspected and a position of an alignment visual target image T obtained from a cornea of the eye to be inspected. In this structure, the imaging portion is greatly moved if the alignment deviation amount is large, while the imaging portion is moved small if the alignment deviation amount is small, so as to improve alignment operability.

However, in the structure disclosed in Japanese Patent Application Laid-Open No. 2001-037722, no consideration is made for a case in which an alignment deviation amount between the eye to be inspected and the imaging portion cannot be detected. The case in which the alignment deviation amount cannot be detected is, specifically, a case in which the visual target image T to be obtained from the eye to be inspected cannot be detected because of blinking, insufficient eye opening, a small pupil, or the like.

It is needless to say that, if a position of the eye to be inspected cannot be detected, a feedback to the operation member cannot be performed, and hence improvement of operability cannot be expected. In other words, it is hitherto essential to detect a position of the eye to be inspected when performing alignment, and there is high possibility that uncomfortable operation feeling occurs depending on success or failure in the detection or on time necessary for the detection.

SUMMARY OF THE INVENTION

The present invention has been made in view of the circumstances described above, and it is an object of the present invention to provide an ophthalmologic apparatus and a control method therefor with which operating accuracy can be improved without determining a positional deviation of an eye to be inspected so that comfortable operation feeling can be obtained.

In order to solve the above-mentioned problem, according to one embodiment of the present invention, there is provided an ophthalmologic apparatus, including:

- an inspection unit configured to obtain inspection information of an eye to be inspected;
- an operation unit configured to operate movement of the inspection unit with respect to a base unit in accordance with an operation amount;
- a moving unit configured to move the inspection unit in accordance with the operation amount input from the operation unit;
- a detection unit configured to detect a position of the inspection unit with respect to the base unit; and
- a control unit configured to control an amount related to movement of the inspection unit corresponding to the operation amount based on a detection result of the detection unit.

According to one embodiment of the present invention, it is possible to provide the ophthalmologic apparatus and the control method therefor with which operating accuracy is improved without determining the positional deviation of the eye to be inspected so that comfortable operation feeling is obtained.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

First Embodiment

As an ophthalmologic instrument as one embodiment of the present invention, a fundus camera to which the present invention is applied is described in detail with reference to FIG. 1 to FIGS. 7A and 7B.

An ophthalmologic apparatus according to an embodiment of the present invention includes an inspection unit configured to obtain inspection information of an eye to be inspected, a base unit including a support member for determining a holding position of the eye to be inspected, an operating portion configured to operate movement of the inspection unit with respect to the base unit in accordance with an operation amount, a moving unit configured to move the inspection unit in accordance with the operation amount input from the operating portion, a detection unit configured to detect a position of the inspection unit with respect to the base unit, and a control unit configured to control an amount related to movement of the inspection unit corresponding to the operation amount based on a detection result of the detection unit. In this way, a speed and moving amount per operation amount are switched so that alignment can be performed comfortably in accordance with a position of an imaging portion 7 as the inspection unit. For instance, because a fine operation is necessary in a vicinity of the eye to be inspected, the speed and moving amount per operation amount are small. Thus, improvement of operation accuracy can be expected. In addition, in contrast, if a large positional movement is necessary, for example, in an area apart from the eye to be inspected, the speed and moving amount per operation amount are large, and hence reduction in operation time necessary for imaging can be expected. Therefore, operation accuracy can be improved to obtain comfortable operation feeling without determining a positional deviation of the eye to be inspected.

Figure 1:
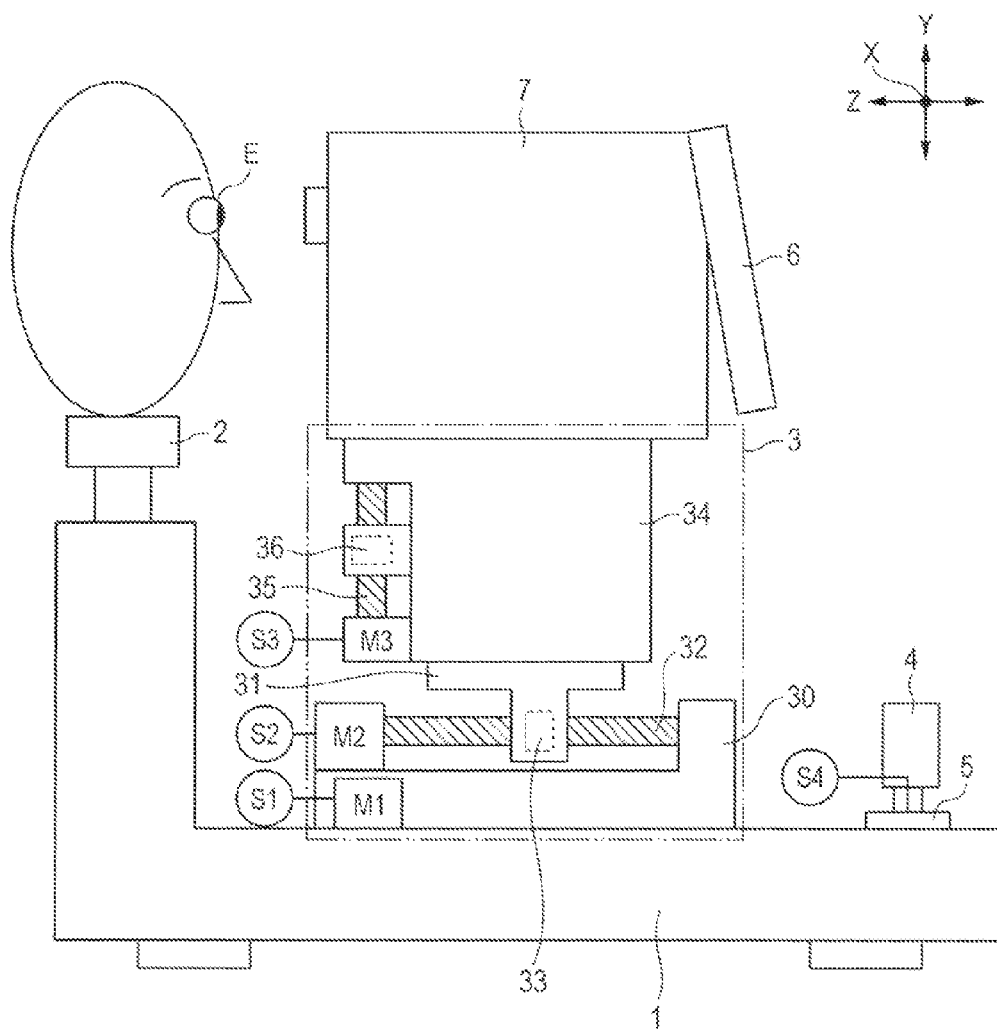
FIG. 1 is an overall view of a fundus camera according to a first embodiment of the present invention.

FIG. 1 is an overall view of the fundus camera according to the first embodiment of the present invention.

This fundus camera includes a base unit 1, a chin rest portion 2, a drive unit 3, an alignment operation member 4, a focus operation member 5, a display portion 6, and the imaging portion 7. The chin rest portion 2 is supported in a vertically movable manner (in the up and down direction in FIG. 1) with respect to the base unit 1 so as to support a chin of a subject. The base unit 1 is referred to as a fixed basement 1 in this embodiment and is defined as one including the chin rest portion 2 or the like as a support member for determining a holding position of the eye to be inspected. The drive unit 3 is disposed on the fixed basement 1 and is an example of a moving unit of the imaging portion 7 or the like. In the drive unit 3, as an example of a detection unit configured to detect a position of the inspection unit, there are disposed an X axis position sensor S1, a Z axis position sensor S2, and a Y axis position sensor S3. The alignment operation member works as an operating portion and also works as an operation amount detection unit. In addition, the alignment operation member 4 and the focus operation member 5 are mounted to the base unit 1. The imaging portion 7 for imaging the eye to be inspected is an example of the inspection unit configured to take an image of the eye to be inspected for imaging and observing the eye to be inspected. The display portion 6 is fixed to the imaging portion 7 so as to display an image of the eye to be inspected obtained by the imaging portion 7.

An inspector operates the alignment operation member 4 so as to instruct a drive direction, a drive amount, and drive speed of the drive unit 3, and hence the imaging portion 7 and an eye to be inspected E can be aligned with each other. The alignment operation member 4 functions as the operating portion for operating the position or movement of the inspection unit with respect to the base unit 1 in accordance with the operation amount. As described later, in order to move the imaging portion 7 in an X direction that is a left and right direction (a direction perpendicular to the paper plane in FIG. 1 or an eye width direction of the eye to be inspected E), in a Z direction that is a front and back direction (a left and right direction in FIG. 1 or an approaching and separating direction to the eye to be inspected E), and in a Y direction that is an up and down direction (an up and down direction in FIG. 1), the drive unit 3 includes drive mechanisms corresponding to the individual axes. The drive unit 3 moves a position of the inspection unit in accordance with an input from the alignment operation member 4. In addition, when the inspector operates the focus operation member 5, a stop position thereof is detected by a focus operation member position sensor S4.

Further, the display portion 6 is disposed on the imaging portion 7 in this embodiment, but the display portion 6 may be disposed on the fixed basement 1.

[X Axis]

The drive unit 3 includes an X frame 30 capable of moving in the X direction with respect to the fixed basement 1 as a structure for driving the imaging portion 7 in the X direction. The drive mechanism for the X direction included in the drive unit 3 includes an X axis drive motor M1, a feed screw, and a nut. The X axis drive motor M1 is fixed onto the fixed basement 1. A motor output shaft of the X axis drive motor M1 is coupled to the feed screw (not shown), and the nut (not shown) fixed to the X frame 30 moves on the feed screw in the X direction. With this structure, when the X axis drive motor M1 rotates, the X frame 30 moves in the X direction via the feed screw and the nut. The X axis position sensor S1 detects a stop position of the X frame 30.

[Z Axis]

The drive unit 3 includes a Z frame 31 capable of moving in the Z direction with respect to the fixed basement 1 as a structure for driving the imaging portion 7 in the Z direction. The Z frame 31 can move in the Z direction with respect to the X frame 30. A drive mechanism for the Z direction includes a Z axis drive motor M2, a Z feed screw 32, and a Z nut 33. The Z axis drive motor M2 is fixed onto the X frame 30. A motor output shaft of the Z axis drive motor M2 is coupled to the Z feed screw 32, and the Z nut 33 fixed to the Z frame 31 moves on the Z feed screw 32 in the Z direction. When the Z axis drive motor M2 rotates, the Z frame 31 moves in the Z direction via the Z feed screw 32 and the Z nut 33. The Z axis position sensor S2 detects a stop position of the Z frame 31.

[Y Axis]

The drive unit 3 includes a Y frame 34 capable of moving in the Y direction with respect to the fixed basement 1 as a structure for driving the imaging portion 7 in the Y direction. The Y frame 34 can move in the Y direction with respect to the Z frame 31. A drive mechanism for the Y direction includes a Y axis drive motor M3, a Y feed screw 35, and a Y nut 36. The Y axis drive motor M3 is fixed onto the Y frame 34. A motor output shaft of the Y axis drive motor M3 is coupled to the Y feed screw 35, and the Y nut 36 fixed to the Z frame 31 relatively moves on the Y feed screw 35 in the Y direction. When the Y axis drive motor M3 rotates, the Y frame 34 moves in the Y direction via the Y feed screw 35 and the Y nut 36. The Y axis position sensor S3 detects a stop position of the Y frame 34.

[Alignment Operation Member]

Figure 2:
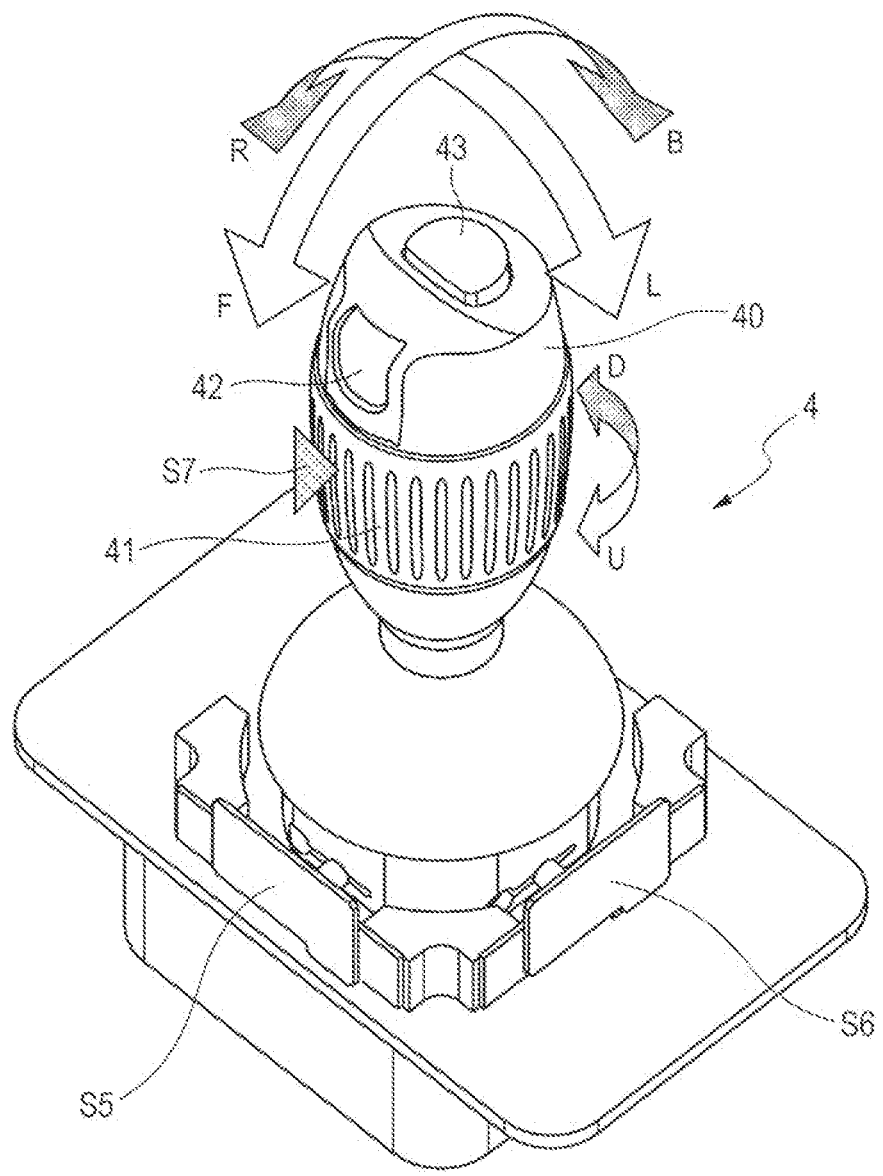
FIG. 2 is a perspective view of an alignment operation member of the fundus camera illustrated in FIG. 1.

FIG. 2 is a perspective view of a joystick as one example of the alignment operation member according to the first embodiment of the present invention.

The alignment operation member 4 includes a joystick 40, a rotation dial 41, an anterior ocular segment observation auxiliary lens operation switch 42, an image pickup switch 43, an X direction alignment operation amount detection sensor S5, and a Z direction alignment operation amount detection sensor S6. The joystick 40 is operated to tilt so as to move the imaging portion 7 in the X direction and in the Z direction. The rotation dial 41 is operated to rotate so as to move the imaging portion 7 in the Y direction. Further, inside the rotation dial 41 disposed to be coaxial with the joystick 40, a Y direction alignment operation amount detection sensor S7 is disposed.

When the inspector operates the joystick 40 to tilt in an LR direction in FIG. 2, a tilt direction and a tilt angle of the joystick 40 are detected as the operation amount by the X direction alignment operation amount detection sensor S5. In response to this operation amount, the imaging portion 7 moves in the X direction. Similarly, when the joystick 40 is operated to tilt in an FB direction, a tilt direction and a tilt angle of the joystick 40 are detected as the operation amount by the Z direction alignment operation amount detection sensor S6. In response to this operation amount, the imaging portion 7 moves in the Z direction. In addition, when the inspector operates the rotation dial 41 to rotate in a UD direction, the Y direction alignment operation amount detection sensor S7 detects a rotation direction and a rotation amount of the rotation dial 41 so that the imaging portion 7 moves in the Y direction.

Figure 3:
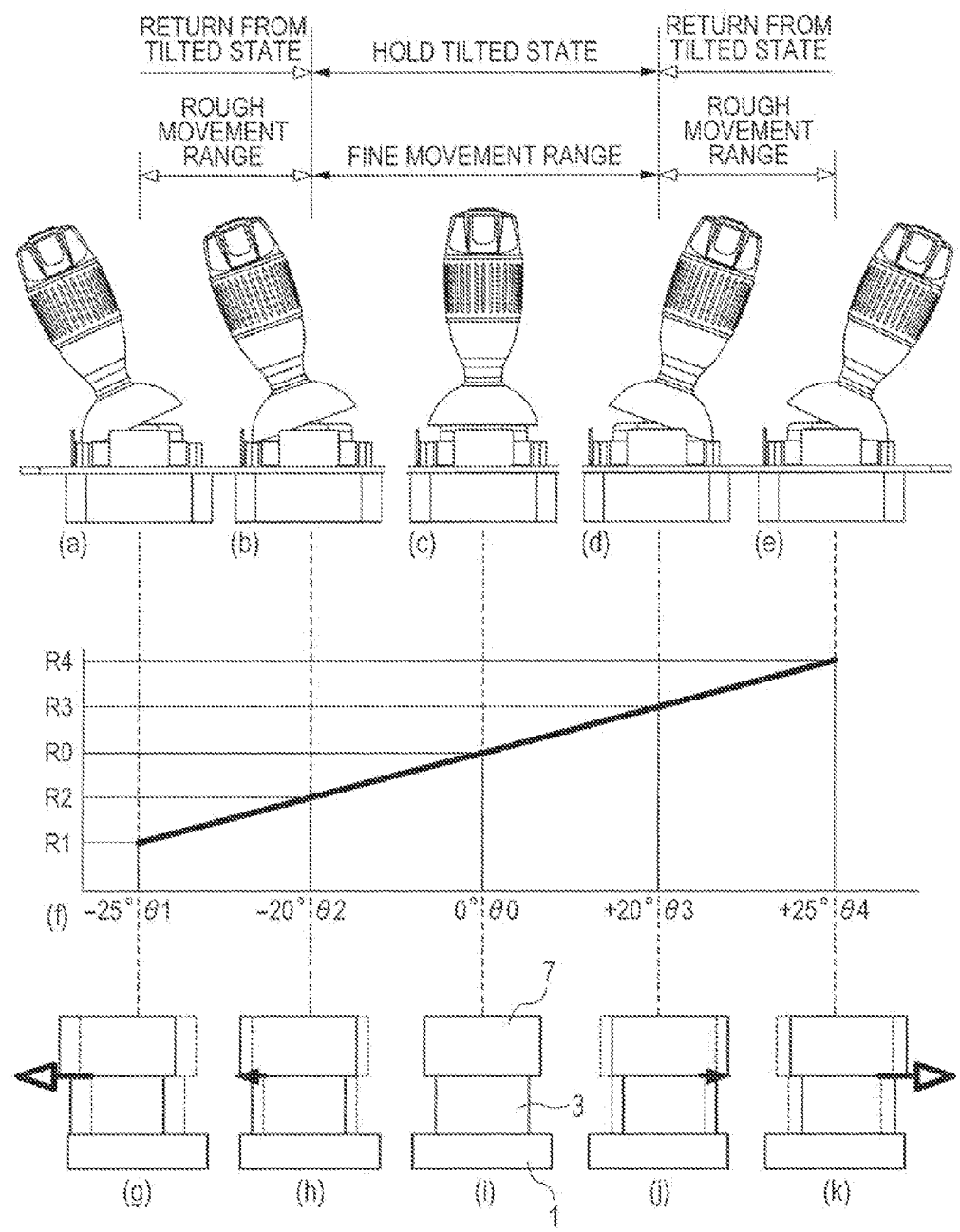
FIG. 3 is a diagram illustrating a relationship between a tilted posture of the alignment operation member and a state of an inspection unit.

FIG. 3 is a diagram illustrating states (a) to (e) indicating postures of the alignment operation member 4 corresponding to tilt angles θ of the joystick 40 in the X direction, a graph (f) indicating a relationship between the tilt angle θ and a resistance value R as an output of the X direction alignment operation amount detection sensor S5, and states (g) to (k) indicating corresponding movements of the imaging portion 7, in an associated manner.

Here, the tilt angles are, for example, θ1 is −25°, θ2 is −20°, θ0 is 0°, θ3 is +20°, and θ4 is +25°. Further, resistance values R1, R2, R0, R3, and R4 correspond to the tilt angles θ1, θ2, θ0, θ3, and θ4, respectively.

In an area where the joystick 40 is within a range of the tilt angles θ2 to θ3 (−20° to +20°) corresponding to a range of the resistance values R2 to R3, the tilt angle of the joystick 40 is held. In this case, a system control portion 100 illustrated in FIG. 5 performs positional control for driving of the X axis drive motor M1 based on an output of the X direction alignment operation amount detection sensor S5, which changes along with the tilt angle of the joystick 40. In other words, it is possible to perform fine movement for moving the imaging portion 7 finely.

On the other hand, in an area where the joystick 40 is within a range of the tilt angles θ1 to θ2 (−25° to −20°) corresponding to a range of the resistance values R1 to R2 and in an area where the joystick 40 is within a range of the tilt angles θ3 to θ4 (+20° to)+25° corresponding to a range of the resistance values R3 to R4, the tilt angle of the joystick 40 returns to a predetermined angle θ2 or θ3. In this case, the system control portion 100 performs speed control for driving of the X axis drive motor M1 based on an output of the X direction alignment operation amount detection sensor S5, which changes along with the tilt angle of the joystick 40. In other words, it is possible to perform rough movement for greatly moving the imaging portion 7.

[Optical System]

Figure 4:
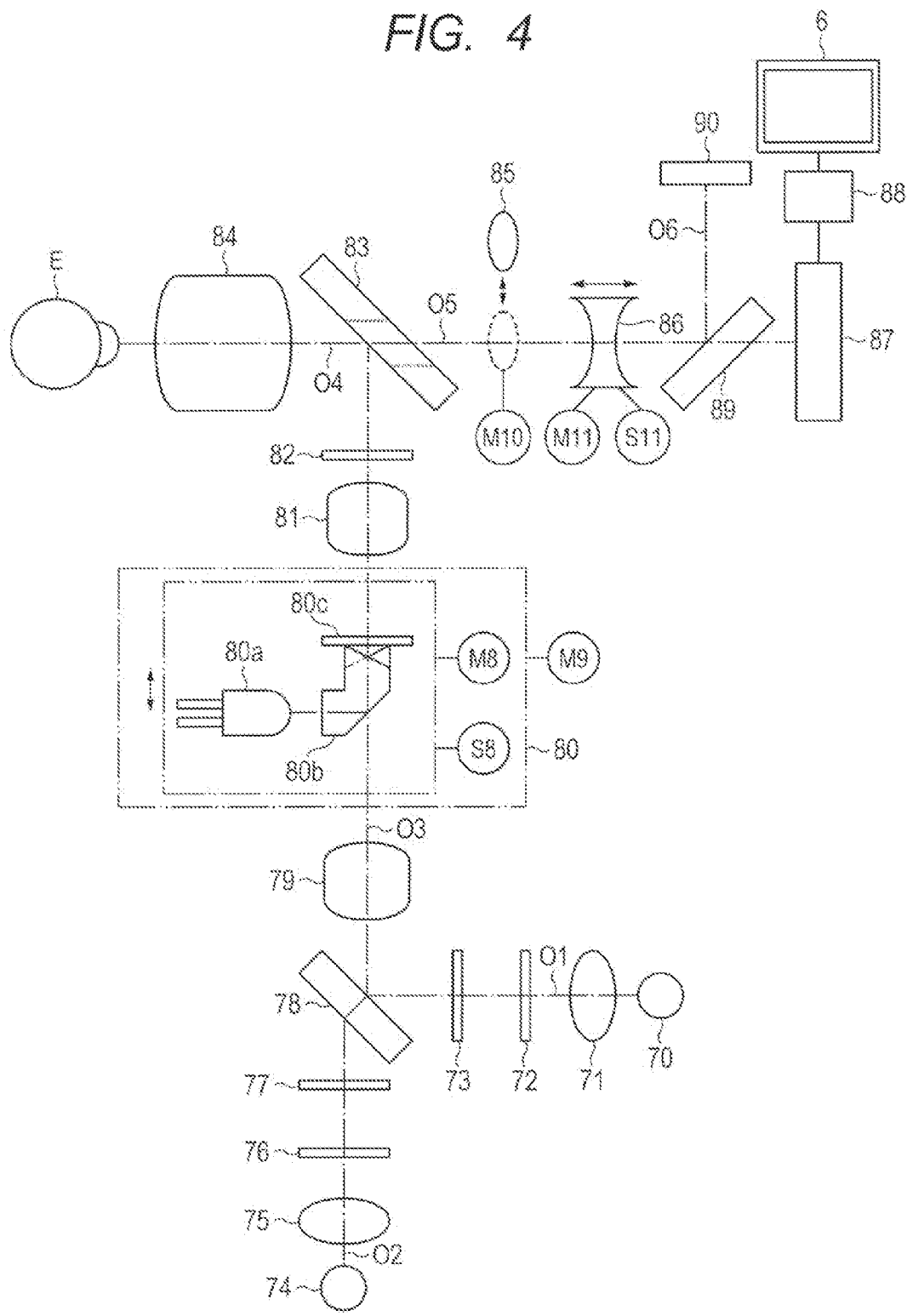
FIG. 4 is a diagram illustrating a structure of an optical system of an imaging portion of the fundus camera illustrated in FIG. 1.

FIG. 4 is a structural diagram of an optical system of the imaging portion according to the first embodiment of the present invention.

The imaging portion 7 includes an imaging light source portion O1, an observation light source portion O2, an illumination optical system O3, an imaging/illumination optical system O4, an imaging optical system O5, and an inner fixation target portion O6. A light beam emitted from the imaging light source portion O1 or the observation light source portion O2 passes through the illumination optical system O3 and the imaging/illumination optical system O4, and illuminates the eye to be inspected E. An image of the eye to be inspected E is formed on an image pickup element after passing through the imaging/illumination optical system O4 and the imaging optical system O5.

The imaging light source portion O1 has the following structure. An imaging light source 70 emits light when a voltage is applied to Xe filled in a glass tube, and can provide sufficient intensity of white color light necessary for recording a fundus image when imaging is performed. An imaging condenser lens 71 is an ordinary spherical lens. An imaging ring slit 72 is a flat plate having an annular aperture. An imaging lens baffle 73 is also a flat plate having an annular aperture. A light beam emitted from the imaging light source 70 is condensed by the imaging condenser lens 71 toward the fundus and is shaped into an annular shape by the imaging ring slit 72 before passing through the anterior ocular segment. In addition, the imaging lens baffle 73 limits light beams projected to the lens of the eye to be inspected so as to prevent a ghost image of reflection light from the lens of the eye to be inspected, which is unnecessary for the fundus image.

The observation light source portion O2 has the following structure. An observation light source 74 is a light source such as a halogen lamp or an LED capable of continuously emitting light, and emits infrared light by element characteristics or using an optical filter. An observation condenser lens 75 is an ordinary spherical lens. An observation ring slit 76 is a flat plate having an annular aperture. An observation lens baffle 77 is also a flat plate having an annular aperture. The observation light source portion O2, which is different from the imaging light source portion O1 only in a type of the light source, condenses light by the observation condenser lens 75, shapes the light beams before the anterior ocular segment by the observation ring slit 76, and prevents a ghost image of reflection light from the lens in the fundus image by the observation lens baffle 77.

The light beams emitted from the imaging light source portion O1 and the observation light source portion θ2 are relayed by the illumination optical system O3, and an index image for focusing of the fundus image is added. A dichroic mirror 78 transmits infrared light and reflects visible light. The dichroic mirror 78 reflects the light beams of visible light emitted from the imaging light source portion O1 and transmits the light beams of infrared light emitted from the observation light source portion O2 so as to be guided to the illumination optical system O3. The ring-shaped illumination light forms an image on the eye to be inspected E by a first illumination relay lens 79 and a second illumination relay lens 81.

A split unit 80 includes a focus index light source 80a for projecting a focus index, a prism 80b for splitting the light source, and a focus index mask 80c indicating an external shape of the focus index. In addition, the split unit 80 further includes a moving mechanism for moving the focus index to shift in the optical axis direction by inserting those structures into the illumination optical system O3 and moving the structures in an arrow direction in FIG. 4 during observation, and an insert/withdraw mechanism for withdrawing those structures from the illumination optical system O3 during imaging. A split shift drive motor M8 and a split position sensor S8 drive the split unit 80 to shift for adjusting focus of the focus index and detect a stop position thereof. In addition, a split insert/withdraw drive motor M9 inserts or withdraws the split unit 80 into or from the illumination optical system O3. The split insert/withdraw drive motor M9 is controlled, during observation of a fundus, to insert the split unit 80 into the illumination optical system O3 so as to project a split index to the observed image, and is controlled, during imaging, to withdraw the split unit 80 from the illumination optical system O3 so as to prevent the focus index from being a ghost image in the taken image. A cornea baffle 82 prevents reflection light from the cornea of the eye to be inspected from being a ghost image, which is unnecessary for the fundus image.

The imaging/illumination optical system O4 projects illumination light beams to the eye to be inspected E and extracts reflection light beams from the eye to be inspected. A perforated mirror 83 has a mirror part in a periphery and a center aperture. The light beams guided from the illumination optical system O3 are reflected by the mirror part and illuminate the eye to be inspected E through an objective lens 84. The reflection light beams from the eye to be inspected E return through the objective lens 84, pass through the center aperture of the perforated mirror 83, and are extracted to the imaging optical system O5.

The imaging optical system O5 adjusts focus of a fundus image of the eye to be inspected and forms the image on the image pickup element. An anterior ocular segment observation auxiliary lens 85 for increasing magnification is driven by an anterior ocular segment observation auxiliary lens insert/withdraw drive motor M10 to be inserted into the imaging optical system O5 during observation of the anterior ocular segment, and to be withdrawn from the imaging optical system O5 during observation of the fundus. Further, the anterior ocular segment observation auxiliary lens may also work as a diopter correction lens for severe hyperopia (not shown).

A focus lens 86 is a lens for performing focus adjustment of the imaging light beams and moves in an arrow direction in FIG. 4 so as to perform focus adjustment. A focus lens drive motor M11 and a focus lens position sensor S11 drive the focus lens 86 for focus adjustment and detect a stop position thereof. An image pickup element 87 performs photoelectric conversion of the imaging light. An electrical signal obtained by the image pickup element 87 is AD converted by an image processing portion 88 to be digital data and is displayed on the display portion 6 when infrared observation is performed. After the imaging, the digital data is recorded in a recording medium (not shown).

An optical path of light from the inner fixation target portion O6 is split by a half mirror 89 from the imaging optical system O5, and an inner fixation target unit 90 is opposed to the optical path. The inner fixation target unit 90 includes a plurality of LEDs, and an LED at a position corresponding to a fixation part selected by the inspector is lighted. When the subject stares at the lighted LED, the inspector can obtain a fundus image in a desired direction.

[Control System]

Figure 5:
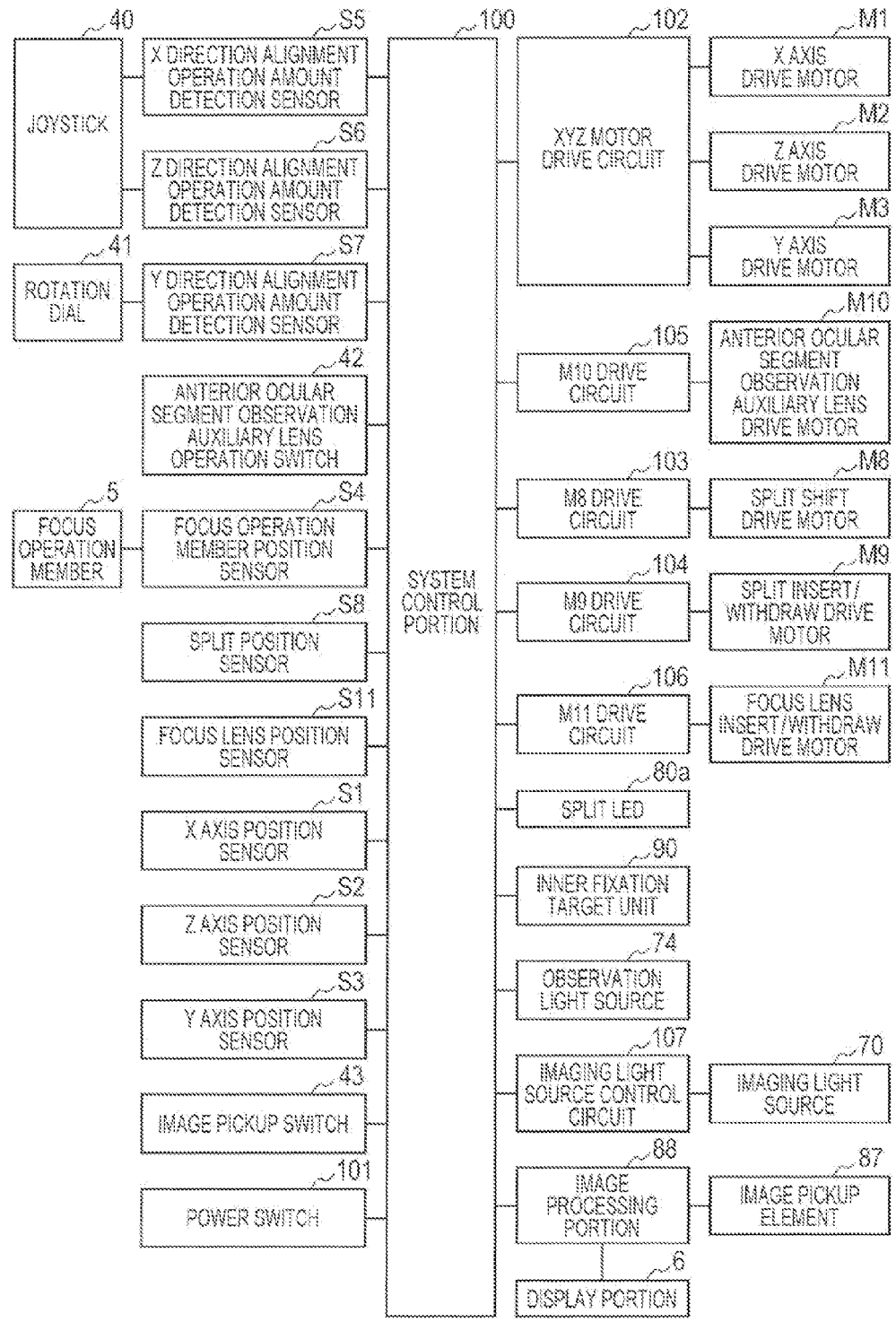
FIG. 5 is an electrical block diagram of the fundus camera illustrated in FIG. 1.

FIG. 5 is an electrical block diagram illustrating the first embodiment of the present invention.

The system control portion 100 controls all the following operations of the fundus camera according to the first embodiment. A power switch 101 is a switch for selecting a power supply state of the fundus camera. An XYZ motor drive circuit 102 drives the X axis drive motor M1, the Z axis drive motor M2, and the Y axis drive motor M3. Those motors are controlled so that the imaging portion 7 moves to a position corresponding to an output of each of the X direction alignment operation amount detection sensor S5, the Z direction alignment operation amount detection sensor S6, and the Y direction alignment operation amount detection sensor S7.

An M10 drive circuit 105 drives the anterior ocular segment observation auxiliary lens drive motor M10 so that the anterior ocular segment observation auxiliary lens 85 is inserted into or withdrawn from the imaging optical system O5 in response to operation of the anterior ocular segment observation auxiliary lens operation switch 42. In addition, also when the Z axis position sensor S2 detects that the imaging portion 7 greatly moves to the inspector side, the anterior ocular segment observation auxiliary lens drive motor M10 is driven so that the anterior ocular segment observation auxiliary lens 85 is inserted into the imaging optical system O5. An M8 drive circuit 103 drives the split shift drive motor M8 so that the split unit 80 moves to a position corresponding to an output of the focus operation member position sensor S4. An M9 drive circuit 104 drives the split insert/withdraw drive motor M9 so that the split unit 80 is inserted into or withdrawn from the illumination optical system O3 before or after the imaging. Similarly to the M8 drive circuit 103, an M11 drive circuit 106 drives the focus lens drive motor M11 so that the focus lens 86 moves to a position corresponding to an output of the focus operation member position detection sensor S4. An imaging light source control circuit 107 charges energy for the imaging light source 70 to emit light before imaging, and discharges the charged electrical energy in the imaging so that the imaging light source 70 emits light.

[Positional and Speed Control of Imaging Portion for Unit Operation Amount]

Here, with reference to FIGS. 6A and 6B and FIGS. 7A and 7B, positional and speed control of the imaging portion 7 based on the operation by the alignment operation member 4 are described, which is a feature of the present embodiment. Note that, distribution between the positional control and the speed control described later is an example. The positional control and the speed control can be used independently or together, in accordance with a determined area described later. By using the control appropriately, it can be expected that usability as the ophthalmologic instrument is improved. Therefore, the moving amount and the moving speed of the inspection unit are exemplified as amounts related to movement.

Figure 6A:
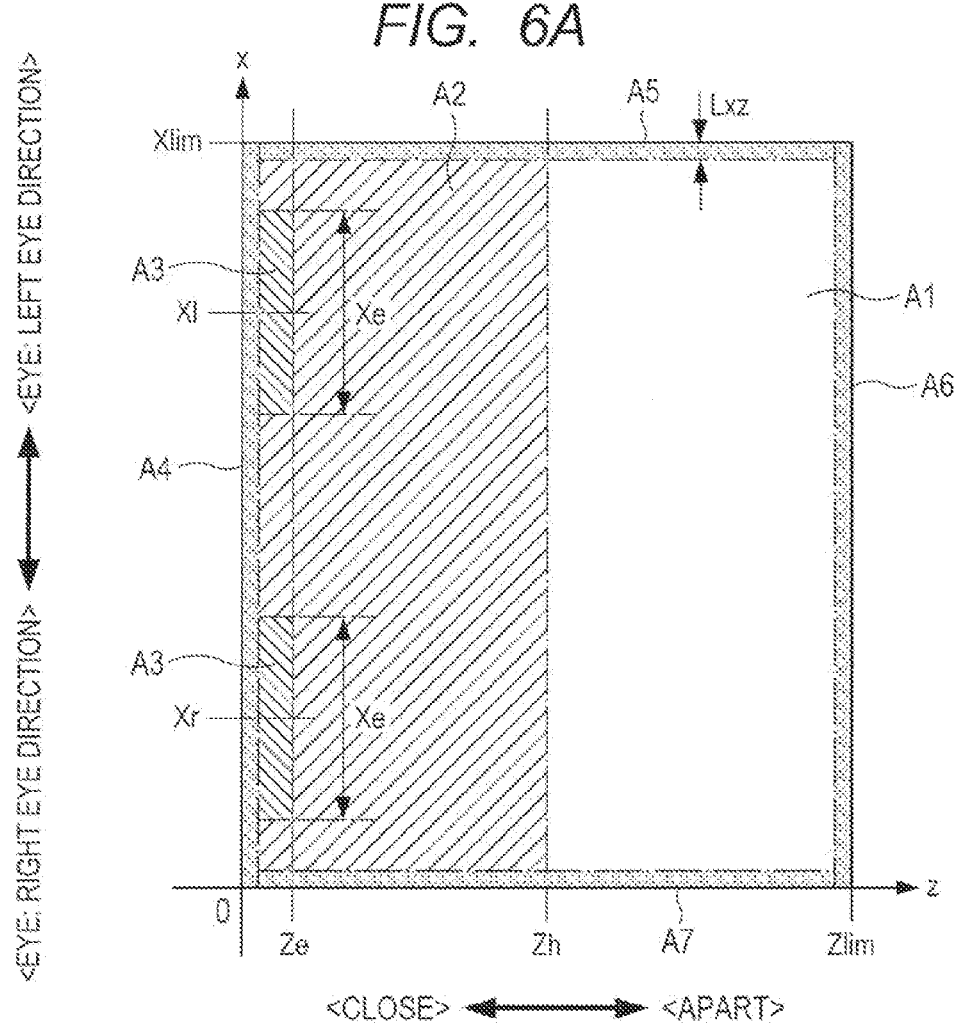
FIGS. 6A and 6B are diagrams illustrating classification of speed and moving amount areas of the inspection unit according to the first embodiment.
Figure 6B:
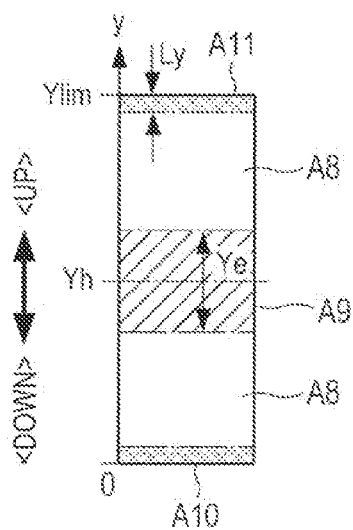

FIGS. 6A and 6B illustrate area classification of the speed and moving amount of the inspection unit according to the first embodiment of the present invention.

FIG. 6A illustrates area classification in the XZ coordinate system.

An origin (0, 0) in the XZ coordinate system is set as a position when, in a movable range of the imaging portion 7, the imaging portion 7 moves closest to a direction from a right eye to be inspected toward a left eye to be inspected in the X coordinate and moves closest to the eye to be inspected in the Z coordinate. The imaging portion 7 can move from the origin to Xlim in the X coordinate and to Zlim in the Z coordinate. Xlim, Zlim, and Ylim described later correspond to boundaries as limits of the movable range in the present invention. Here, the center of the chin rest portion 2 is at a position of Xlim/2 in the X coordinate. Further, in the first embodiment, Xlim is set to 105 mm, and Zlim is set to 70 mm. In addition, a position of the imaging portion 7 in the XZ coordinate system is detected by the X axis position sensor S1 and the Z axis position sensor S2.

In addition, in the first embodiment, the movable range from (0, 0) to (Xlim, Zlim) in the XZ coordinates is divided into seven areas A1 to A7. The individual areas have different operation amounts of the alignment operation member 4, namely different speeds and moving amounts of the imaging portion 7 corresponding to the tilt angle of the joystick 40.

First, ranges of the areas A1 to A7 are described. The speed and moving amount corresponding to operation in each area are described later. An eye-to-be-inspected apart area A1 is a range obtained by subtracting, from a range from Zh to Zlim in the Z coordinate, a left eye-to-be-inspected side moving limit neighboring area A5, an eye-to-be-inspected apart moving limit neighboring area A6, and a right eye-to-be-inspected side moving limit neighboring area A7, which are described later. In this embodiment, Zh=Zlim/2 holds. Because it is estimated that the imaging portion 7 is apart from the eye to be inspected in the eye-to-be-inspected apart area A1, the drive speed and the moving amount of the imaging portion 7 corresponding to the unit operation amount are determined to be largest.

A rough alignment area A2 is a range obtained by subtracting, from a range from 0 to Zh in the Z coordinate, a fine alignment area A3, an eye-to-be-inspected neighboring moving limit neighboring area A4, the left eye-to-be-inspected side moving limit neighboring area A5, and the right eye-to-be-inspected side moving limit neighboring area A7, which are described later. If the imaging portion 7 is in the rough alignment area A2, it is estimated that the operator is performing rough alignment in which the imaging portion 7 is roughly aligned with the eye to be inspected E. Therefore, the drive speed and the moving amount of the imaging portion 7 corresponding to the unit operation amount are determined to be smaller than those in the eye-to-be-inspected apart area A1.

The fine alignment area A3 is a range obtained by subtracting the eye-to-be-inspected neighboring moving limit neighboring area A4 described later from a range of a width Xe with a center of Xl or Xr in the X coordinate and 0 to Ze in the Z coordinate. Here, Xl, Xr, and Xe are values calculated statistically from a positional relationship between chin and eye of a plurality of persons. The values are determined so that when the subject puts the chin on the chin rest 2, the pupil position is substantially within a range of Xe with a center of Xl for the left eye and Xr for the right eye. The values Xl and Xr are also positions at which the alignment is estimated to be finished by the fine alignment and are handled as reference positions of the inspection unit at which the alignment is estimated to be finished in the present invention. The reference positions are statistic values calculated in advance as described above and are determined based on a relative position between the inspection unit (imaging portion 7) and the base unit (fixed basement 1). In addition, the fine alignment area A3 is determined by a determination unit as an area of a predetermined range including the reference position or with reference to the reference position.

In the first embodiment, Xl and Xr are disposed symmetrically with respect to the center of the movable range, and a distance between Xl and Xr is 65 mm. Further, Xe is determined to 75 mm, and Ze is determined to 30 mm. When the imaging portion 7 is within the fine alignment area A3, it is estimated that the operator is performing the fine alignment in which the imaging portion 7 and the eye to be inspected E are finely aligned. Therefore, the speed and the moving amount of the imaging portion 7 corresponding to the unit operation amount are determined smaller than those in the rough alignment area A2. Alternatively, more simply, it is sufficient to determine the amount related to movement to be smaller when the inspection unit is within the fine alignment area A3 than when the inspection unit is outside the fine alignment area A3.

The eye-to-be-inspected neighboring moving limit neighboring area A4 is a range of a predetermined width from 0 to Lxz in the Z coordinate. In this range neighboring the moving limit of the imaging portion 7, drive corresponding to the operation in the direction toward moving limit, namely to the subject side is limited. This is aimed at preventing damage to the drive mechanism when the imaging portion 7 reaches a moving limit end at high speed.

Similarly, the left eye-to-be-inspected side moving limit neighboring area A5 is a range from Xlim-Lxz to Xlim in the X coordinate, and the amount related to movement as drive corresponding to the operation, to the left direction from the subject, namely in a direction toward the movable range limit is restricted.

Similarly, the apart area side moving limit neighboring area A6 is a range from Zlim-Lxz to Zlim in the Z coordinate, and the drive corresponding to the operation to the direction apart from the subject is restricted.

Similarly, the right eye-to-be-inspected side moving limit neighboring area A7 is a range from 0 to Lxz in the X coordinate, and the drive corresponding to the operation to the right direction from the subject is restricted.

In the first embodiment, a dimension Lxz determining each moving limit neighboring area range corresponding to the moving limit is determined to 5 mm.

FIG. 6B illustrates area classification in a Y coordinate system.

An origin 0 in the Y coordinate system is set as a position when the imaging portion 7 is in the lowest position in the Y coordinate. The imaging portion 7 can move from the position relatively to Ylim in the Y coordinate. In the first embodiment, Ylim is 7 mm. In addition, a position of the imaging portion 7 in the Y coordinate system is detected by the Y axis position sensor S3.

In this embodiment, the movable range from 0 to Ylim in the Y coordinate is divided into four areas A8 to A11. The individual areas have different moving amounts of the imaging portion 7 corresponding to the operation amount of the alignment operation member 4, namely the rotation amount of the rotation dial 41. First, ranges of the areas A8 to A11 are described. The moving amount in each area corresponding to the operation is described later.

A height rough alignment area A8 is a range obtained by subtracting a height fine alignment area A9, a lower side moving limit neighboring area A10, and an upper side moving limit neighboring area A11 described later from the entire movable range. When the imaging portion 7 is within the height rough alignment area A8, it is estimated that the operator is performing rough alignment in which the imaging portion 7 is roughly aligned with the eye to be inspected E. Therefore, the moving amount of the imaging portion 7 corresponding to the unit operation amount is determined to be largest.

The height fine alignment area A9 is a range having a width Ye with a center Yh in the Y coordinate. Here, Yh=Ylim/2 holds. The position of Yh with respect to a plane of the chin rest portion 2 on which the chin is placed is an average value of height of the eye from the chin calculated from a positional relationship between chin and eye of a plurality of persons. The value is determined so that when the subject puts the chin on the chin rest 2 that is at the average position, the pupil position of the eye to be inspected is substantially within a range of the width Ye with the center Yh in a statistic manner. In other words, similarly to the above-mentioned Xl and Xr, Yh is a reference position in the height direction, which is determined based on a relative position between the inspection unit and the base unit. In the first embodiment, a projection distance to the Y coordinate between Yh and a plane of the chin rest portion 2 on which the chin is placed is determined to 13 mm. In addition, Ye is 3 mm.

If the imaging portion 7 is within the height fine alignment area A9, it is estimated that the operator is performing fine alignment in which the imaging portion 7 is finely aligned with the eye to be inspected E. Therefore, the moving amount of the imaging portion 7 corresponding to the unit operation amount is determined to be smaller than that in the height rough alignment area A8.

The lower side moving limit neighboring area A10 is a range from 0 to Ly in the Y coordinate. Similarly to the moving limit neighboring area described above, the drive corresponding to the operation of lowering the imaging portion 7 is restricted.

The upper side moving limit neighboring area A11 is a range of a predetermined width from Ylim-Ly to Ylim in the Y coordinate. The drive corresponding to the operation for lifting the imaging portion 7 is restricted. Further, in this embodiment, Lxz and Ly are values having the same predetermined width, but it is possible that Lxz and Ly have different values in accordance with inspection content or a requirement of the ophthalmologic equipment.

The plurality of areas described above are plurality of areas defined by a relative position between the inspection unit and the base unit 1, and determining of these areas is performed by a module region of the system control portion 100 working as the determination unit. In addition, the amount related to movement such as the moving speed or the moving amount of the inspection unit is controlled in accordance with the operation amount of the alignment operation member, and correspondence therebetween is changed in accordance with the area determined by the determination unit, in which the inspection unit is positioned. In addition, the control concerning the operation amount corresponding to this area and the position related to movement is performed by a module region of the system control portion 100 working as the control unit.

Figure 7A:
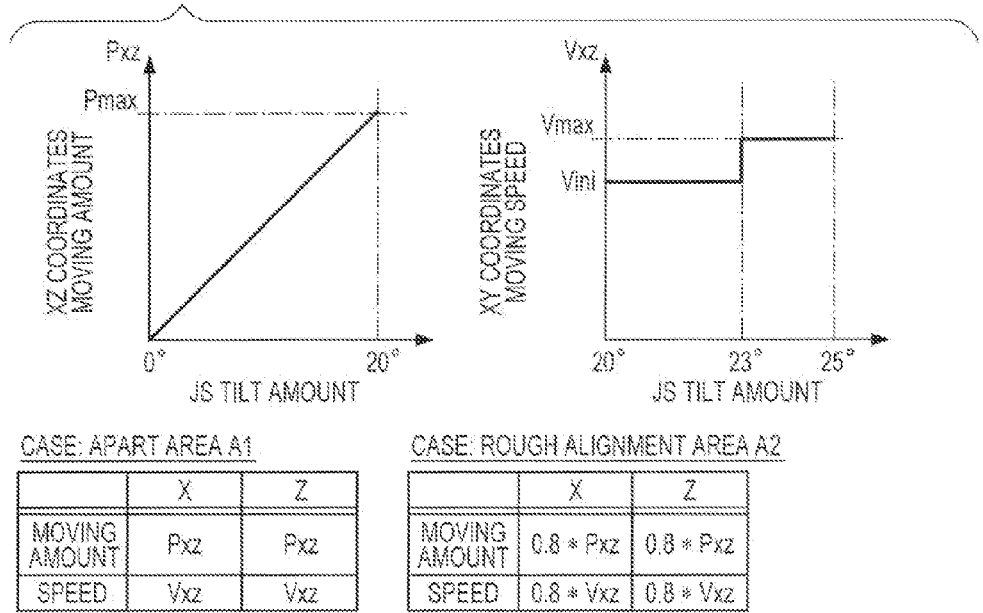
FIGS. 7A and 7B are diagrams illustrating speeds and moving amounts of areas exemplified in FIGS. 6A and 6B in an associated manner.
Figure 7B:
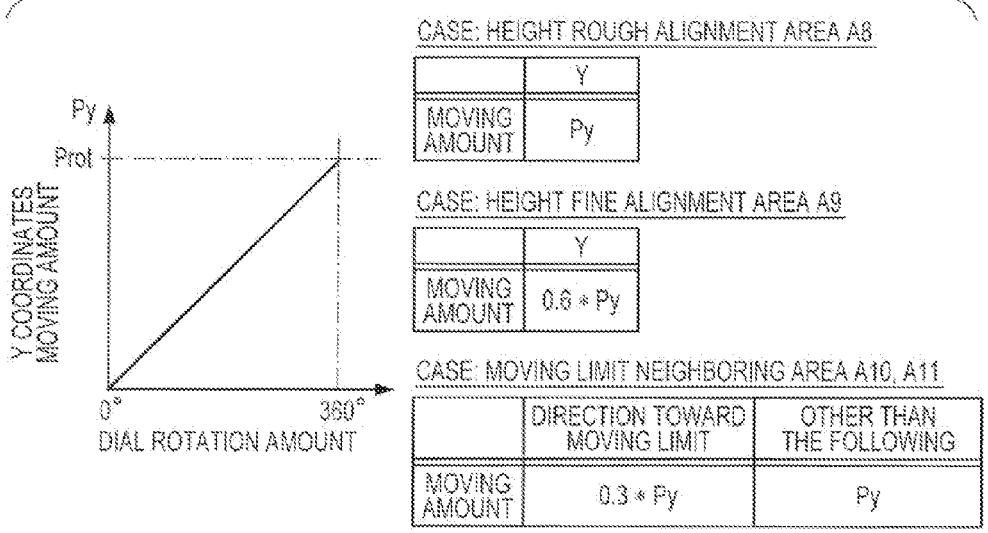

Here, with reference to FIGS. 7A and 7B, the speed and moving amount of the imaging portion 7 corresponding to the operation amount in the above-mentioned areas A1 to A11 are described.

FIG. 7A is a diagram illustrating control of the speed and moving amount corresponding to the operation amount in the XZ coordinate system.

First, for describing drive control, the drive speed and the moving amount of the imaging portion 7 corresponding to the unit operation amount in the eye-to-be-inspected apart area A1 are described. As described above with reference to FIG. 3, the position of the imaging portion 7 is changed by positional control in the range of the tilt amount from 0° to 20° of the joystick 40, and is changed by speed control in the range of the tilt amount from 20° to 25°. In the positional control, the movement is proportional to the tilt angle, and the moving amount becomes the largest value Pmax at a tilt angle of 20°. In addition, in the range of a tilt angle of the joystick 40 from 20° to 23°, the drive control of the imaging portion 7 is performed by the speed control, and the operating portion 7 moves at a speed Vini. In the tilt angle of the joystick 40 from 23° to 25°, the imaging portion 7 moves at a speed Vmax.

In the rough alignment area A2, the moving amount and speed corresponding to the tilt angle of the joystick are determined to 80% of those in the eye-to-be-inspected apart area A1.

In the fine alignment area A3, the moving amount and speed corresponding to the tilt angle of the joystick 40 are determined to 60% and 40%, respectively, of those in the eye-to-be-inspected apart area A1.

In each of the moving limit neighboring areas A4 to A7, as to the operation to move the imaging portion 7 in the direction toward moving limit, the moving amount corresponding to the tilt angle of the joystick 40 is determined to 60% of that in the eye-to-be-inspected apart area A1. In addition, without accepting the operation to perform the speed control, when the joystick 40 is tilted by 20° or larger in the direction toward moving limit, the imaging portion 7 moves corresponding to the tilt angle 20° and stops. In addition, as to an operation to drive the imaging portion 7 in a direction other than the direction toward moving limit, the drive is performed in accordance with the speed and moving amount in other neighboring areas.

FIG. 7B is a diagram illustrating control of the speed and moving amount corresponding to the operation amount in the Y coordinate system.

First, for describing the drive control, the moving amount corresponding to the operation in the height rough alignment area A8 is described. The imaging portion is driven to move up and down in proportion to the rotation amount of the rotation dial 41. The moving amount of the imaging portion 7 per turn of the rotation dial is Prot.

In the height fine alignment area A9, the moving amount corresponding to the rotation amount of the rotation dial 41 is determined to 60% of that in the height rough alignment area A8.

In the lower side moving limit neighboring area A10 and the upper side moving limit neighboring area A11, as to the operation to drive the imaging portion 7 in the direction toward moving limit, the moving amount corresponding to the rotation amount of the rotation dial is determined to 30% of that in the height rough alignment area A8. As to the operation to drive the imaging portion 7 in the direction opposite to the direction toward moving limit, the drive is performed by the same moving amount as that in the height rough alignment area A8.

According to the fundus camera having the structure described above, the speed and moving amount per operation amount are switched so that alignment can be comfortably performed in accordance with a position of the imaging portion 7 as the inspection unit. For instance, in a vicinity of the eye to be inspected, because the fine operation is necessary, the speed and moving amount per operation amount become small. In this way, improvement of operation accuracy can be expected. In addition, in contrast, in an area apart from the eye to be inspected, in which a large positional movement is necessary, the speed and moving amount per operation amount become large, and hence reduction of operation time necessary for imaging can be expected. Therefore, regardless of detection of the position of the eye to be inspected, comfortable operation feeling can be stably realized.

Second Embodiment

A basic structure of an ophthalmologic apparatus according to a second embodiment of the present invention is the same as that of the first embodiment. As a difference, the image processing portion 88 illustrated in FIG. 5 has a function of detecting the pupil of the eye to be inspected E from the image. The system control portion 100 changes the speed and the position control amount corresponding to the operation amount in accordance with a result of the pupil position detection by the image processing portion 88.

When the pupil is detected, it is determined that the operator is performing the rough alignment in which the imaging portion 7 is roughly aligned with the eye to be inspected E, and the speed and moving amount corresponding to the operation amount are determined to the same values as those in the rough alignment area A2 in the first embodiment regardless of a position of the imaging portion 7. In other words, the speed and the moving amount are determined to 80% of those in the eye-to-be-inspected apart area A1.

If the pupil is not detected, similarly to the first embodiment, the speed and moving amount per operation amount are changed in accordance with the detection result of the position of the imaging portion 7.

In addition, only the pupil position is detected in this embodiment, but it is possible to detect a positional deviation between a position of the eye to be inspected and a position of the imaging portion, and to change the amount related to the positional control per unit operation amount in accordance with the positional deviation. If the positional deviation cannot be detected, the speed and the moving amount per operation amount are changed in accordance with the detection result of the position of the imaging portion 7.

The area determined by the determination unit includes the rough alignment area, in which the amount related to movement is controlled by the control unit so that the rough alignment between the inspection unit and the base unit is performed. In this embodiment, the control unit determines that the inspection unit is within the rough alignment area in accordance with a result of the operation performed so that the inspection unit can obtain a predetermined image of the eye to be inspected. Further, this determination is performed by a module region of the system control portion 100 working as a unit configured to perform the determination.

Alternatively, it is possible to change the amount related to movement in accordance with an output from an eye-to-be-inspected position detection unit configured to detect a positional relationship between the eye to be inspected and the inspection unit and an output from an inspection unit position detection unit. If the positional relationship cannot be detected, the amount related to movement is changed in accordance with an output from the detection unit.

According to the fundus camera having the structure described above, based on observation image information in addition to the first embodiment, information of a positional relationship between the fundus camera and the eye to be inspected can be obtained, and hence, based on the obtained information, the speed and moving amount corresponding to the operation amount are determined. Therefore, improvement of the effect described above in the first embodiment can be expected. In addition, even if the position of the eye to be inspected cannot be detected, such as when the subject does not exist, when the eye to be inspected does not exist in the image acquiring range, or when the eye to be inspected cannot be detected due to blinking, insufficient eye opening, or a small pupil, it is possible to realize comfortable operation feeling similarly to the first embodiment.

Third Embodiment

A basic structure of an ophthalmologic apparatus according to a third embodiment of the present invention is the same as that of the first embodiment. As a difference, there is disposed a subject information input portion (not shown) capable of inputting subject information such as an ID or a name for the operator to identify the subject. When the operator inputs the subject information before imaging, the system control portion 100 records the position of the imaging portion 7 in imaging together with the subject information in a recording portion (not shown) when the imaging is finished.

When imaging again the subject whose subject information is recorded in the past, the operator can retrieve the subject information from the recording portion (not shown). Here, the system control portion 100 refers to the position of the imaging portion 7 in the last imaging, and optimizes the coordinates Xr, Xl, and Yh illustrated in FIGS. 6A and 6B for this subject only for imaging of this subject. In other words, the X coordinate of the imaging portion 7 in the last imaging of the right eye is substituted into Xr. In addition, similarly, the X coordinate of the imaging portion 7 in the last imaging of the left eye is substituted into Xl. In addition, the Y coordinate of the imaging portion 7 in the last imaging is substituted into Yh.

In other words, it is preferred that the system control portion 100 include a module region working as a recording unit configured to record, as the position information, an output of the detection unit configured to detect an inspection unit position when the inspection information of the eye to be inspected is obtained, and change the area determined by the determination unit in accordance with the position information recorded by the recording unit. In addition, it is more preferred that the control unit in this case change the amount related to movement in accordance with the position information recorded by the recording unit and the output from the detection unit.

According to the fundus camera having the structure described above, the speed and moving amount corresponding to the operation amount are switched in accordance with the area classification optimized for the individual positions of the eye to be inspected. In this way, even if the position of the eye with respect to the chin of the subject is deviated from an average value, comfortable operability can be obtained similarly to the first embodiment.

Further, in the embodiments described above, there is described the case where the joystick is used as the alignment operation member, but the present invention is not limited to the case. In other words, it is also possible to use a so-called track ball, a mouse, or the like, which is used in the same manner as the joystick, as the alignment operation member. In addition, the fundus camera is exemplified as the ophthalmologic instrument, but the present invention can also be applied to various types of ophthalmologic instruments using a manual operation member such as a joystick for alignment. Specifically, the present invention can also be applied to a so-called OCT, a tonometer, a pachymeter, a refractometer, a keratometer, and the like. Therefore, it is desired that information obtained by the inspection unit from the eye to be inspected include various images including an image for alignment and be defined as the inspection information.

Further, the present invention is also implemented by executing the following processing. Specifically, in processing according to one embodiment of the present invention, software (program) for implementing the functions of the above-mentioned embodiments is supplied to a system or an apparatus via a network or various kinds of storage medium, and a computer (or CPU, MPU, etc.) of the system or the apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-126729, filed Jun. 17, 2013, which is hereby incorporated by reference herein in its entirety.

What is claimed is:
1. An ophthalmologic apparatus, comprising:
an inspection unit configured to obtain inspection information of an eye to be inspected;
an operation unit configured to operate movement of the inspection unit with respect to a base unit in accordance with an operation amount;

a moving unit configured to move the inspection unit in accordance with the operation amount input from the operation unit;

a detection unit configured to detect a position of the inspection unit with respect to the base unit; and a control unit configured to control an amount related to movement of the inspection unit corresponding to the operation amount based on a detection result of the detection unit.

2. An ophthalmologic apparatus according to claim 1, further comprising a determination unit configured to determine a plurality of areas defined based on a relative position between the inspection unit and the base unit, wherein the control unit controls the amount related to movement of the inspection unit corresponding to the operation amount in accordance with the position of the inspection unit detected by the detection unit and each of the plurality of areas determined by the determination unit in which the inspection unit is positioned.

3. An ophthalmologic apparatus according to claim 2, wherein the each of the plurality of areas determined by the determination unit includes a fine alignment area having a predetermined range including a reference position of the inspection unit at which alignment is estimated to be finished, and wherein the control unit determines the amount related to movement to be smaller when the inspection unit is within the fine alignment area than the amount related to movement when the inspection unit is outside the fine alignment area.

4. An ophthalmologic apparatus according to claim 2, wherein the each of the plurality of areas determined by the determination unit includes a rough alignment area in which the control unit controls an amount related to movement for performing rough alignment between the inspection unit and the base unit, and wherein the control unit comprises a unit configured to determine that the inspection unit is within the rough alignment area in accordance with a result of an operation performed by the inspection unit for obtaining a predetermined image of the eye to be inspected.

5. An ophthalmologic apparatus according to claim 2, further comprising a recording unit configured to record an output of the detection unit when the inspection information of the eye to be inspected is obtained as position information, wherein the control unit changes the each of the plurality of areas determined by the determination unit in accordance with the position information recorded by the recording unit.

6. An ophthalmologic apparatus according to claim 5, wherein the control unit changes the amount related to movement in accordance with the position information recorded by the recording unit and the output from the detection unit.

7. An ophthalmologic apparatus according to claim 2, wherein the determination unit determines a range having a predetermined width from a movable range limit of the inspection unit as a moving limit neighboring area, and wherein the control unit limits the amount related to movement of the inspection unit in a direction toward the movable range limit in the moving limit neighboring area.

8. An ophthalmologic apparatus according to claim 1, wherein the control unit determines the amount related to movement to be smaller when the detection unit detects that the position of the inspection unit is close to the eye to be inspected than the amount related to movement when the detection unit detects that the position is apart from the eye to be inspected.

9. An ophthalmologic apparatus according to claim 1, further comprising an eye-to-be-inspected position detection unit configured to detect a positional relationship between the eye to be inspected and the inspection unit, wherein the control unit changes the amount related to movement in accordance with an output from the eye-to-be-inspected position detection unit and an output from the detection unit, and wherein when the eye-to-be-inspected position detection unit fails to detect the positional relationship, the control unit changes the amount related to movement in accordance with the output from the detection unit.

10. An ophthalmologic apparatus according to claim 1, wherein the operation unit comprises a joystick.

11. An ophthalmologic apparatus according to claim 1, wherein the amount related to movement comprises a moving amount of the inspection unit.

12. An ophthalmologic apparatus according to claim 1, wherein the amount related to movement comprises a moving speed when the inspection unit is moved.

13. An ophthalmologic apparatus according to claim 1, wherein the base unit includes a support member configured to determine a holding position of the eye to be inspected.

14. A control method for an ophthalmologic apparatus, comprising:

detecting a position of an inspection unit configured to obtain inspection information of an eye to be inspected with respect to a base unit;

operating movement of the inspection unit with respect to the base unit in accordance with an operation amount of an operation unit; and controlling an amount related to movement of the inspection unit corresponding to the operation amount based on the detected position of the inspection unit.

15. A control method for an ophthalmologic apparatus according to claim 14, further comprising determining, in a plurality of areas, a range in which the inspection unit moves based on a relative position between the inspection unit and the base unit, wherein the operating of the movement comprises controlling the amount related to movement in accordance with each of the plurality of determined areas.

16. A control method for an ophthalmologic apparatus according to claim 14, wherein the operating movement comprises determining the amount related to movement to be smaller when the position of the inspection unit is detected to be close to the eye to be inspected than the amount related to movement when the position is detected to be apart from the eye to be inspected.

17. A non-transitory tangible medium having recorded thereon a program for causing a computer to perform steps of the control method according to claim 14.

* * * * *